United States Patent [19]
Davies

[11] Patent Number: 6,010,912
[45] Date of Patent: Jan. 4, 2000

[54] ANTENATAL SCREENING FOR CHROMOSOMAL ABNORMALITIES

[75] Inventor: Christopher John Davies, Caerphilly, United Kingdom

[73] Assignee: Johnson & Johnson Clinical Diagnostics, Inc., Rochester, N.Y.

[21] Appl. No.: 08/566,467

[22] Filed: Dec. 4, 1995

Related U.S. Application Data

[63] Continuation of application No. 08/256,320, filed as application No. PCT/EP93/03296, Nov. 24, 1993, abandoned.

[30] Foreign Application Priority Data

Nov. 28, 1992 [GB] United Kingdom ............... 9224965

[51] Int. Cl.$^7$ .................................................. G01N 33/68
[52] U.S. Cl. ........................... 436/510; 436/65; 436/86; 436/87; 436/811; 436/817; 436/818; 705/2
[58] Field of Search .................. 436/65, 86, 87, 436/131, 510, 518, 811, 817, 818; 364/413.09; 705/2

[56] References Cited

U.S. PATENT DOCUMENTS

| | | | |
|---|---|---|---|
| 4,874,693 | 10/1989 | Bogart | 435/7 |
| 5,100,806 | 3/1992 | Macri | 436/518 |
| 5,252,489 | 10/1993 | Macri | 436/87 |
| 5,258,907 | 11/1993 | Macri | 364/413 |
| 5,840,586 | 11/1998 | Davies | 436/510 |

FOREIGN PATENT DOCUMENTS

| | | |
|---|---|---|
| 327337 | 4/1990 | European Pat. Off. . |
| 362294 | 4/1990 | European Pat. Off. . |
| 90/08325 | 7/1990 | WIPO . |

OTHER PUBLICATIONS

Wald et al., Brit. J. Obst. & Gyn., 95, 334–341, 1988.
Wald et al., Brit.Med. J., 297, 883–887, 1988.
Reynolds et al., Ann. Clin. Biochem., 27, 452–458, 1989.
Kratzer et al., Am.J. Hum. Genet., 51, (4 (4 Suppl.), 1992, P. A268, Abstract 1057.
Tim Reynolds and Rhys John: "Comparison of Assay Kits for Unconjugated Estriol Show That Expressing Results as Multiples of the Median Causes Unacceptable Variation in Calculated Risk Factors for Down Syndrome", Clin. Chem. 38:9, pp. 1888–1893, 1992.
Tim Reynolds et al.: "Utility of Unconjugated Estriol in Screening for Down Syndrome is Not Proven", Clin. Chem., 39:9, pp. 2023–2025, 1993.
H.S. Cuckle, Clinical Chemistry, 38, 1687–1689, 1992.
Stabile et al, Prenatal Diagnosis, 8, 387–391, 1988.

*Primary Examiner*—David Saunders

[57] ABSTRACT

A method for antenatal screening for chromosomal abnormalities in which maternal blood from a pregnant woman is measured for levels of free beta hCG and at least a second serum marker and/or precursors and metabolites of these markers and the measured levels of these markers together with the gestational age of the pregnant woman are compared to reference values at various gestational ages of the levels for free beta hCG and the second serum marker in (a) pregnant women carrying foetuses having the abnormalitie(s) subject to the screen and (b) pregnant women carrying normal foetuses, the comparison being indicative of the risk of the pregnant woman carrying a foetus with an abnormality subject to the screen characterised in that the second serum marker is pregnancy associated plasma protein A (PAPPA) and the screen is carried out by the end of the thirteenth (13th) completed week of pregnancy.

4 Claims, 3 Drawing Sheets

ANTENATAL SCREENING FOR CHROMOSOMAL ABNORMALITIES

This is a continuation of application Ser. No. 08/256,320, filed Jun. 28, 1994 and now abandoned, which is hereby incorporated by reference which is a 371 of PCT/EP93/03296 filed Nov. 24, 1993.

This invention relates to a method for antenatal screening for chromosomal abnormalities and to an assay kit for performing the method and in particular to a method and kit for antenatal screening for Down's Syndrome.

The risk of Down's Syndrome and some other chromosomal abnormalities in a foetus is known to increase with the age of the mother and it is this knowledge which forms the basis for selection of pregnant women for further investigation. Further investigation for instance in the case of Down's Syndrome involves sampling of the amniotic fluid by amniocentesis, a procedure which itself carries a risk for the mother or the foetus, induction of a miscarriage being a recognised hazard of this procedure.

Maternal serum markers for Down's Syndrome are widely used for antenatal screening for this chromosomal abnormality, the most common of these markers being alpha-fetoprotein (AFP), human chorionic gonadotropin (hCG)—either the intact molecule thereof or its beta subunit—and unconjugated estriol (uE). Disclosures relating to the use of these markers in antenatal screening for Down's Syndrome include U.S. Pat. No. 4,874,693, WO 89/00696 and WO 90/08325. U.S. Pat. No. 5,100,806 discloses the use of the beta subunit of hCG as a marker in antenatal screening for Edwards Syndrome.

Maternal serum screening is based on selecting a subgroup of women who are at the greatest risk of giving birth to a child with an abnormality, in whom the risks of an invasive diagnostic procedure are considered to be outweighed by the risk of the abnormality. The risk is calculated by multiplying the a priori age related risk by the likelihood ratio. The likelihood ratio is calculated from the relative heights of the multivariate Gaussian distribution functions of marker analytes in affected and unaffected pregnancies, corresponding to the value of the individual serum marker concentrations.

Since the concentrations of the various analytes vary normally with gestational age, the analyte concentrations must be corrected. Correction is performed by dividing the concentration of the analyte by the median concentration expected for that particular gestational age in women with unaffected pregnancies. This is termed the multiple of the median (MoM).

The use of two or more markers together in antenatal screening can be advantageous. For example the markers AFP, hCG and uE can be used together. The combination of marker analytes gives significantly more information than is given by any single marker alone, or by the group of markers when used sequentially. The use of likelihood ratios derived from a multivariate combination is an efficient means of deriving information relating to a woman's risk of carrying an affected child.

Present methods of antenatal screening using maternal serum markers which are in regular use, or are likely to come into regular use in the near future, rely on screening during the second trimester of pregnancy, that is approximately between 14 and 26 weeks.

However maternal serum screening in the first trimester of pregnancy, that is up to 14 weeks, offers considerable advantages over screening in the second trimester. In the first trimester the bonding between the mother and the foetus is less strong than in the second trimester and hence there is less psychological impact should the foetus be affected. In addition the methods of pregnancy interuption are much less traumatic and are safer to the mother in the first trimester than are those available in the second trimester, particularly the late second trimester, that is approximately 18 to 25 or 26 weeks. It is in the late second trimester that several of the present methods for antenatal screening need to be performed.

Thus it is desirable to develop methods of antenatal screening for chromosomal abnormalities using two or more maternal serum markers together which can readily be performed in the first trimester of pregnancy.

According to the present invention we provide a method for antenatal screening for chromosomal abnormalities in which maternal blood from a pregnant woman is measured for levels of free beta hCG and at least a second serum marker and/or precursors and metabolites of these markers and the measured levels of these markers together with the gestational age of the pregnant woman are compared to reference values at various gestational ages of the levels for free beta hCG and the second serum marker in (a) pregnant women carrying foetuses having the abnormality(ies) subject to the screen and (b) pregnant women carrying normal foetuses, the comparison being indicative of the risk of the pregnant woman carrying a foetus with an abnormality subject to the screen characterised in that the second serum marker is pregnancy associated plasma protein A (PAPPA) and the screen is carried out by the end of the thirteenth (13th) completed week of pregnancy.

Further according to the present invention we provide an assay kit for performing a method for antenatal screening for chromosomal abnormalities comprising means for assaying a sample of maternal blood for levels of free beta hCG and at least a second serum marker and/or precursors and of these markers characterised in that the second serum marker is pregnancy associated plasma protein A (PAPPA) and the blood sample is taken by the end of the thirteenth (13th) completed week of pregnancy.

Further according to the prsent invention we provide an apparatus comprising means adapted for receiving measurements of a pregnant woman's maternal blood levels of free beta hCG and at least a second serum marker and/or precursors and metabolites of these markers and computer means for comparing the measurements of these levels to sets of reference data to determine fetal chromosomal abnormalities characterised in that the second serum marker is pregnancy associated plasma protein A (PAPPA) and the measurements are made on a blood sample taken by the end of the thirteenth (13th) completed week of pregnancy.

The method of the invention can be used for antenatal screening for a wide range of chromosomal abnormalities. The most significant and frequently occurring of these is Down's Syndrome (Trisomy 21). Other abnormalities which may be screened for using the invention include Edwards Syndrome (Trisomy 18), Pateaus Syndrome (Trisomy 13), Turner Syndrome, Monosomy X and Kleinefelter's Syndrome. The method of the invention may be used to screen for individual abnormalities or to screen for groups of abnormalities together, for example it could be used to screen for both Down's Syndrome and Edwards Syndrome.

The method of the invention can be used to measure other serum markers in blood samples in addition to hCG and PAPPA. Such other markers include alpha-fetoprotein (AFP), unconjugated estriol (uE), inhibin (In), progesterone (Pr), 16-alpha-hydroxy-dehydroepiandrosterone sulphate (16-alpha-hydroxy-DHEAS) and dehydroepiandrosterone sulphate (DHEAS) and precursors and metabolites of these markers. Thus one or more of these other markers may be measured together with the principal markers of the assay kit of the invention. For example the method of the invention may be used with hCG, PAPPA and AFP as the markers to be measured.

Measurements are carried out using the method of the invention on blood samples taken during the first trimester of pregnancy, i.e. up to the end of the thirteenth completed week of gestation. Preferably the measurements are made on blood samples taken in the period between the beginning of the eighth week and the end of the thirteenth week of gestation (8th to 13th weeks). The woman's measured serum value for the individual serum marker is divided by the expected median value found in women with unaffected pregnancies at the same gestational age, to derive the (MoM). The probability that the (MoM) values for the combination of serum markers tested belongs to the multivariate distribution of values found in unaffected pregnancies is calculated. The same calculation is performed by reference to the probability that the individual combination of values forms part of the multivariate distribution found in abnormal pregnancies. The ratio of the two probabilities is termed the likelihood ratio (LR) which indicates the likelihood that an individual woman has an affected pregnancy or not. The degree of separation between the multivariate distributions for affected and unaffected pregnancies changes with gestational age, i. e. there is a continuous change in the manner of calculating probability depending upon the gestational age. This continuous change can be built into the algorithm used in the calculation.

An individual woman has an a priori age related risk which is independent of the maternal serum marker concentrations. The woman's age related risk, by Baye's theorum, is modified by multiplying by the likelihood ratio (LR) obtained previously to derive a combined risk. This combined risk may then be used to counsel the woman regarding the relative risk of the abnormality as opposed to the risk of miscarriage associated with a subsequent diagnostic invasive procedure.

In the first trimester of pregnancy the concentration of the free beta subunit of hCG is higher in women with a Down's Syndrome foetus and lower in women carrying a foetus with Edwards Syndrome (Trisomy 18). Conversely the levels of PAPPA are lower than normal in women carrying children with either Down's Syndrome or Trisomy 18 during the first trimester of pregnancy. This makes it very suitable to combine measurements of PAPPA and free beta hCG in to a bivariate distribution for both affected and unaffected pregnancies in order to calculate the risk of a woman carrying an affected child in the first trimester.

The invention is illustrated by the accompanying drawings wherein.

Figure 1:
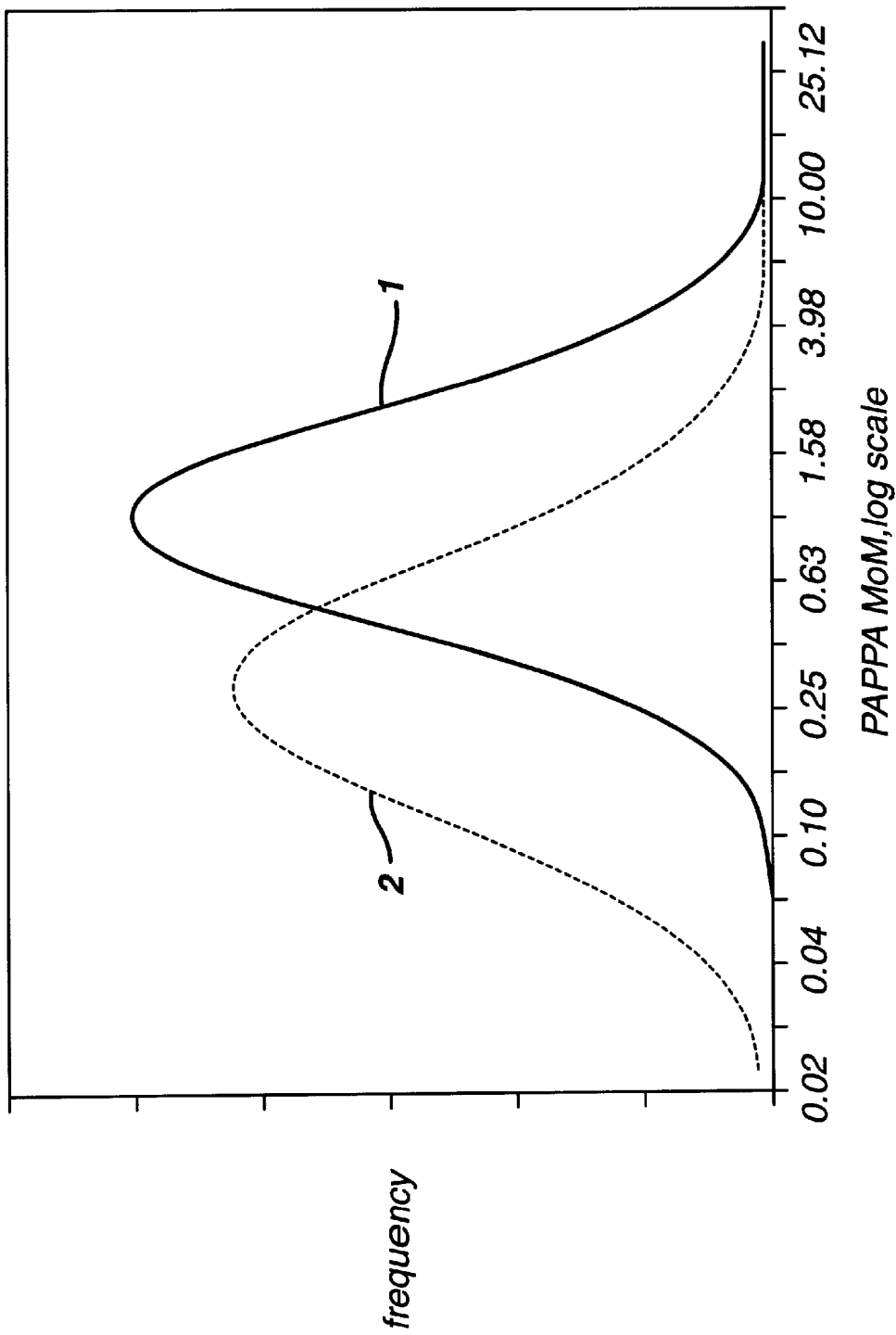
FIG. 1 is a graph of Frequency against PAPPA MoM on a log scale which shows the frequency distribution of maternal serum PAPPA expressed as MoM in first trimester pregnancies with Down's Syndrome (curve 2) and without Down's Syndrome (curve 1).
Figure 2:
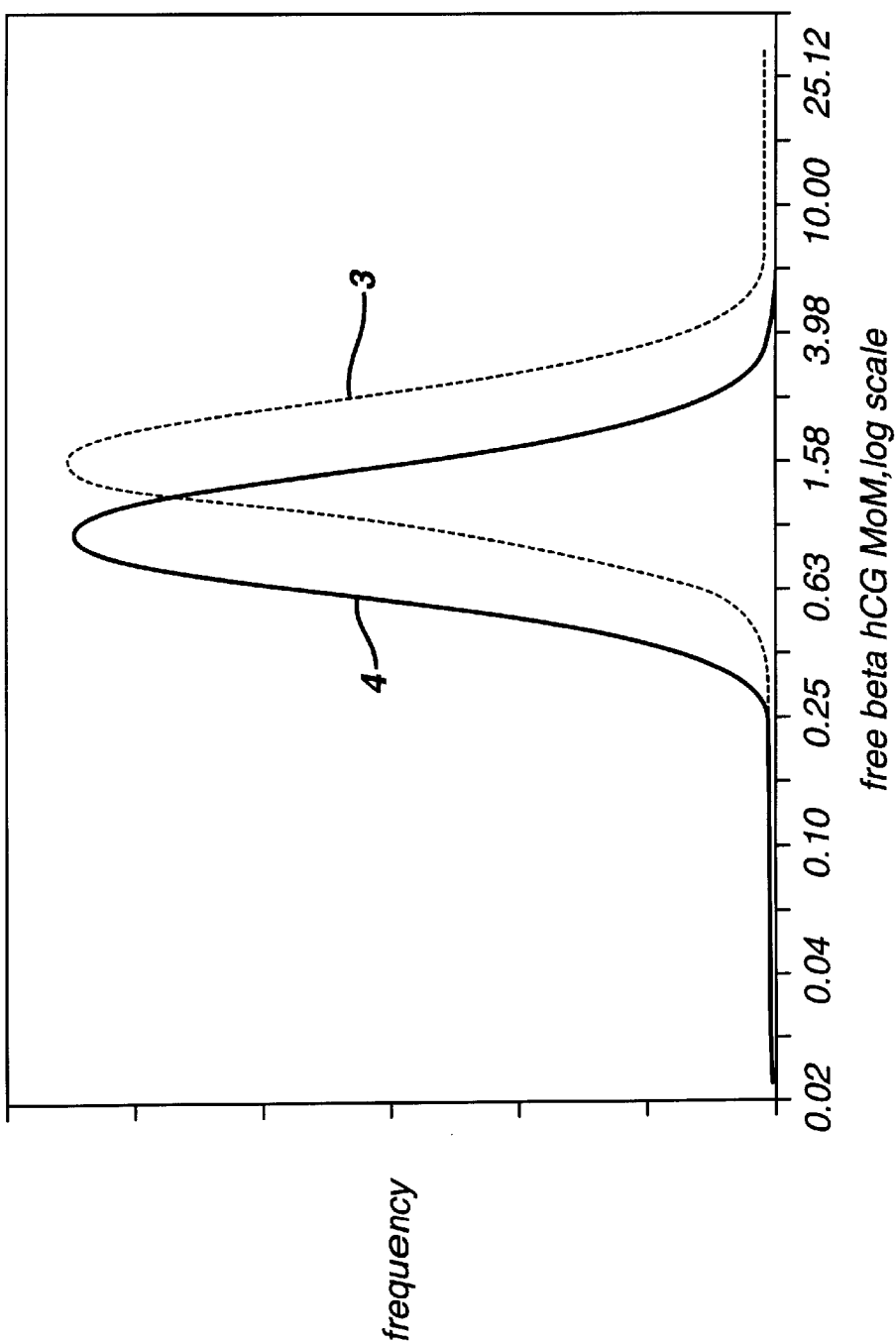
FIG. 2 is a graph of Frequency against free beta hCG MoM on a log scale which shows the frequency distribution of maternal serum free beta hCG expressed as MoM in first trimester pregnancies both with Down's Syndrome (curve 3) and without Down's Syndrome (curve 4).
Figure 3:
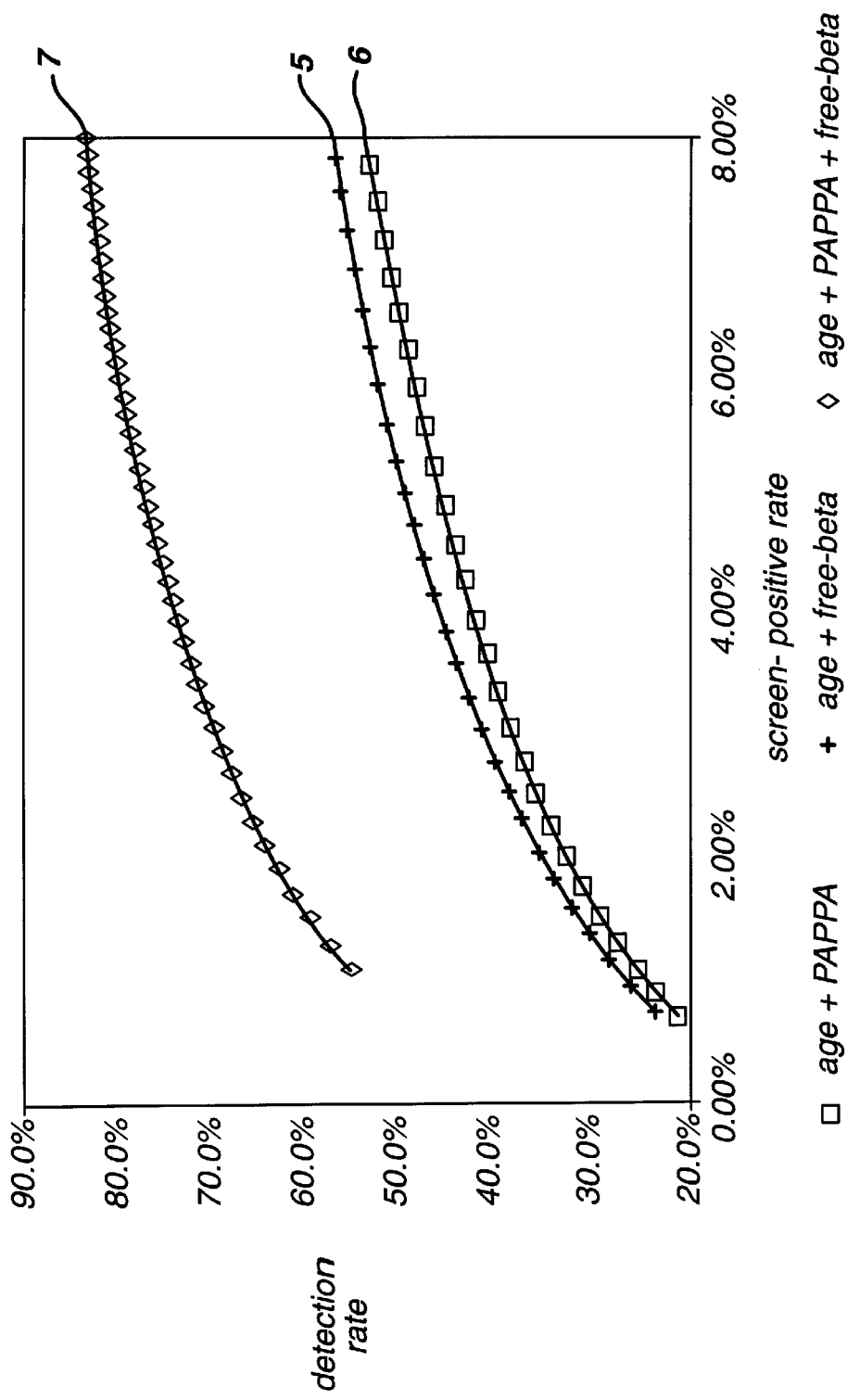

FIG. 3 contains a series of receiver operating characteristic curves showing the relationship between detection rate (the proportion of women whose combined risk of abnormality is greater than a given cut-off risk) and the screen positive rate (which is the proportion of all women, both affected and unaffected who have a combined risk greater than a given cut-off risk). Details of individual curves in FIG. 3 are given later in Example 2.

The invention is illustrated by the following Examples:

EXAMPLE 1

An example of how the combination of PAPPA and free beta hCG may be used to determine an individual woman's risk is shown below, using as an example a woman of 35 years of age.

In the example a number of sequential calculations are performed as follows:

a) The a priori age risk

This is determined from epidemiological survey data relating to a woman's risk of giving birth to a Down's Syndrome child and her age at the date of delivery (Cuckle, H. S., Wald, N. J. and Thompson, S. G., British Journal of Obstetrics and Gynaecology (1987), 94, 387–402).

The risk of giving birth is calculated using the following equation:

$$\text{Age-related risk} = \frac{1 - 0.000627 + e^{(-16.2395 + 0.286 \text{ age}^*)}}{0.000627 + e^{(-16.2395 + 0.286 \text{ age}^*)}}$$

$*=$ maternal age at date of delivery b) Calculation of the multiple of the median value During the first trimester of pregnancy, PAPPA and free beta hCG levels change significantly. To allow for this, all assay results from the mother's serum are first transformed to multiples of the medians to relate the actual result for that analyte to what would be expected for that week of gestation for unaffected pregnancies.

The ratio of an individual woman's assay result to the expected value for the gestational age (estimated to the day) is termed the multiple of the median (MoM) and it is this value which is required for calculation of her risk.

Calculation of the likelihood ratio—the statistical method used to calculate this is trivariate Gaussian frequency distribution analysis. A series of constants are required to calculate the likelihood ratio. These are:

the means and standard deviations of the frequency distributions of PAPPA and free beta hCG (log transformed to ensure Gaussian distribution) for both Down's syndrome and unaffected pregnancies the correlation coefficients between each pair combination of PAPPA and free beta hCG for Down's Syndrome and unaffected pregnancies.

The description of the method used to determine the probability of an unaffected and a Down's Syndrome related pregnancy is described below.

Probability Determinations

For a single assay, the mathematical calculation of the probability is very simple. The probability that a single result is either in the normal range or the Down's Syndrome range is given by:

$$f(x) = \frac{1}{\sigma\sqrt{2\pi}} e^{-\frac{1}{2}(\frac{x-\mu}{\sigma})^2}$$

where $\mu$=transformed population mean for unaffected or affected pregnancies

σ=standard deviation of the transformed populations for unaffected or affected pregnancies X=transformed sample value When a pair of assays is used, the bivariate distribution function set out below is used:

$$f(x, y) = \frac{1}{2\pi\sigma_x\sigma_y\sqrt{1-\rho^2}} e^{-\frac{1}{2}\frac{1}{(1-\rho^2)}\left[\left(\frac{x-\mu_x}{\sigma_x}\right)^2 + \left(\frac{y-\mu_y}{\sigma_y}\right)^2 - \left(2\rho\frac{(x-\mu_x)}{\sigma_x}\frac{(y-\mu_y)}{\sigma_y}\right)\right]}$$

where $\mu_x$=transformed population mean for unaffected or affected pregnancies for analyte x $\mu_y$=transformed population mean for unaffected or affected pregnancies for analyte y $\sigma_x$=standard deviation of the transformed population for unaffected or affected pregnancies for analyte x $\sigma_y$=standard deviation of the transformed population for unaffected or affected pregnancies for analyte y X=transformed sample value, analyte x Y=transformed sample value, analyte y ρ=correlation coefficient between transformed x and y for unaffected or affected pregnancies Calculation of combined risk The final step is the calculation of the combined risk. This is given by the following equation:

Combined Risk=Age related risk×Likelihood ratio

The statistical distributions used for the univariate or bivariate Gaussian distributions for unaffected or Down's Syndrome pregnancies are shown in Table 1. These were derived from a study of 16 first trimester Down's Syndrome samples and 350 unaffected control samples. Log Gaussian univariate and bivariate distributions fitted the data well and the statistical distributions in Table 1 therefore refer to MoM values after natural log transformation.

TABLE 1

|  | Unaffected pregnancies | Down's Syndrome affected pregnancies |
| --- | --- | --- |
| Mean free beta hCG | 0.0000 | 0.8190 |
| Standard deviation (sd) of free beta hCG | 0.6325 | 0.6325 |
| Mean PAPPA | 0.0000 | −0.8723 |
| sd of PAPPA | 0.7222 | 0.7222 |
| Correlation PAPPA vs free beta hCG | 0.3622 | 0.3622 |

All data are expressed as natural logarithms of the multiple of the median (MoM).

The covariances were not statistically significantly different in unaffected and Down's Syndrome affected pregnancies and were therefore pooled as shown above.

The a priori age risk for a 35 year old woman (following Table 1)=1:384.

The risk factors for a 35 year old woman with various levels of free beta hCG and PAPPA are shown in Table 2. This is divided into two sections (respectively 2a and 2b) showing likelihood ratios and final risks.

TABLE 2

|  |  | PAPPA MoM | | |
| --- | --- | --- | --- | --- |
| Free beta hCG MoM | Not Assayed | 0.5 | 1.0 | 2.0 |
| Section 2a - Likelihood ratios | | | | |
| Not Assayed | — | 0.651 | 2.074 | 6.611 |
| 0.5 | 9.558 | 16.268 | 103.712 | 661.170 |
| 1.0 | 2.313 | 1.830 | 11.664 | 74.359 |
| 2.0 | 0.560 | 0.206 | 1.312 | 8.363 |
| Section 2b Final risk (Likelihood ratio × age risk) | | | | |
| Not Assayed | — | 1:250 | 1:796 | 1:2536 |
| 0.5 | 1:3670 | 1:6247 | 1:39825 | 1:253889 |
| 1.0 | 1:888 | 1:703 | 1:4479 | 1:28554 |
| 2.0 | 1:215 | 1:79 | 1:504 | 1:3211 |

The results in Table 2 show that if the result of the first test is known the other result is still informative. For example if a 35 year old woman had a PAPPA level of 1.0 MoM, the a priori age-related risk of 1:384 would be modified to 1:3670 at a free beta hCG level of 0.5 MoM and 1:215 at a free beta hCG level of 2.0 MoM.

EXAMPLE 2

To assess the screening performance realistically in its intended clinical setting it is necessary to simulate the performance when applied to the general screened population.

5000 sets of values were constructed from the univariate and bivariate log Gaussian distributions for unaffected pregnancies described in Table 1 using MINITAB™ (a statistical package).

5000 sets of data corresponding to the distribution for Down's Syndrome affected pregnancies were similarly constructed.

For each sample likelihood ratios were calculated as described in Example 1 univariately for PAPPA and free beta hCG and bivariately using both in combination.

The age distribution of pregnancies in England and Wales for the years 1986–1988 were used as the reference maternal age distribution.

The simulation was performed as follows:

Various risk cut-offs (from 1:100 to 1:500) were examined. For each risk cut-off and for each maternal age (from 11 to 55) the likelihood ratio required to alter the age risk to below that cut-off was calculated. The proportion of likelihood ratios in the 5000 simulated unaffected samples determines the proportion of unaffected women at that age who would be screen positive. The proportion of likelihood ratios in the 5000 simulated Down's Syndrome affected samples determines the proportion of women at that age who would screen positive.

Multiplying the proportions by the actual numbers of women at that age gives the false-positive rate (percentage of unaffected women who screen positive) and the detection rate (percentage of Down's Syndrome affected women who screen positive) at that maternal age.

Summation of the respective numbers over women of all ages gives the overall false positive and detection rates in the entire general population.

Examination of different risk cut-off values enables the construction of a receiver operating characteristic curve (ROC curve) which relates the false positive rate to the detection rate.

The ROC curve is shown in FIG. 3 which shows the relationship between screen positive rate and detection rate using as markers free beta hCG alone+age (curve 5), PAPPA alone+age (curve 6) and a combination of these two markers+age (curve 7). From FIG. 3 it can be seen that when the combination of markers is used the detection rate is increased considerably over that using either marker individually.

Table 3 shows the actual detection rates at various screen positive rates for different combinations of serum markers.

TABLE 3

| MARKERS USED | SCREEN POSITIVE RATE | DETECTION RATE |
|---|---|---|
| Maternal Age | 5.0% | 29.8% |
| Free B hCG + Maternal Age | 5.0% | 49.6% |
| PAPPA + Maternal Age | 5.0% | 45.8% |
| Free B hCG + PAPPA + Maternal Age | 5.0% | 77.3% |

The results in Table 3 show that where free B hCG and PAPPA are combined as serum markers there are significant improvements in detection rates.

I claim:

1. A method for antenatal screening for a chromosomal abnormality in a fetus, comprising:
    A) calculating a pregnant patient's a priori risk of carrying a fetus having said chromosomal abnormality,
    B) measuring said pregnant patient's blood in the first trimester for a concentration of free beta hCG, its precursors and metabolites, or a mixture thereof,
    C) measuring said pregnant patient's blood in the first trimester for a concentration of pregnancy associated plasma protein A, its precursors and metabolites, or a mixture thereof,
    D) calculating a normalized value for each of said concentrations from steps B) and C) by dividing said concentrations by a median value found in a population of women with unaffected pregnancies and same gestational age as said pregnant patient,
    E) calculating a first probability that the normalized values are part of a bivariate Gaussian distribution of values found in pregnancies with said chromosomal abnormality,
    F) calculating a second probability that the normalized values are a part of a bivariate Gaussian distribution of values found in unaffected pregnancies,
    G) calculating a likelihood ratio, said likelihood ratio being the ratio of said first probability and said second probability, and
    H) modifying the a priori risk by the likelihood ratio.

2. The method of claim 1 wherein the chromosomal abnormality is Down's Syndrome.

3. The method of claim 1 wherein the chromosomal abnormality is selected from the group consisting of: Edward's Syndrome, Pateaus Syndrome, Turner Syndrome, Monosomy X, Kleinefelter's Syndrome, and any combination thereof.

4. An apparatus comprising, a means adapted for receiving measurements of a pregnant woman's maternal blood concentration of concentration of free beta hCG, its precursors and metabolites, or a mixture thereof, and a computer programmed to carry out the following activities:
    A) determining a pregnant patient's a priori risk of carrying a fetus having a chromosomal abnormality,
    B) measuring said pregnant patients blood in the first trimester for a concentration of free beta hCG, its precursors and metabolites, or a mixture thereof,
    C) measuring said pregnant patient's blood in the first trimester for a concentration of pregnancy associated plasma protein A, its precursors and metabolites, or a mixture thereof,
    D) calculating a normalized value for each of said concentrations from steps B) and C) by dividing said concentrations by a median value found in a population of women with unaffected pregnancies and same gestational age as said pregnant patient,
    E) calculating a first probability that the normalized values are part of a bivariate Gaussian distribution of values found in pregnancies with said chromosomal abnormality,
    F) calculating a second probability that the normalized values are a part of a bivariate Gaussian distribution of values found in unaffected pregnancies,
    G) calculating a likelihood ratio, said likelihood ratio being the ratio of said first probability and said second probability, and
    H) modifying the a priori risk by the likelihood ratio.

* * * * *